United States Patent
Seppala et al.

(10) Patent No.: US 8,206,431 B2
(45) Date of Patent: *Jun. 26, 2012

(54) STENT BODY SOCK

(75) Inventors: Jan Seppala, Maple Grove, MN (US); Fernando DiCaprio, St. Paul, MN (US); Raed Rizq, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1600 days.

This patent is subject to a terminal disclaimer.

(21) Appl. No.: 11/181,533

(22) Filed: Jul. 14, 2005

(65) Prior Publication Data

US 2005/0251243 A1    Nov. 10, 2005

Related U.S. Application Data

(63) Continuation of application No. 09/970,458, filed on Oct. 2, 2001, now abandoned.

(60) Provisional application No. 60/238,795, filed on Oct. 5, 2000.

(51) Int. Cl.
*A61F 2/06* (2006.01)
*A61F 11/00* (2006.01)

(52) U.S. Cl. ........................ 623/1.12; 623/1.11; 606/108

(58) Field of Classification Search ................. 623/1.11, 623/1.12; 606/108, 191, 194, 198
See application file for complete search history.

(56) References Cited

U.S. PATENT DOCUMENTS

| | | | |
|---|---|---|---|
| 4,950,227 A | 8/1990 | Savin et al. | |
| 5,108,416 A | 4/1992 | Ryan et al. | |
| 5,403,341 A | 4/1995 | Solar | |
| 5,445,646 A * | 8/1995 | Euteneuer et al. | 606/198 |
| 5,534,007 A * | 7/1996 | St. Germain et al. | 623/1.11 |
| 5,944,726 A | 8/1999 | Blaeser et al. | |
| 5,968,069 A | 10/1999 | Dusbabek et al. | |
| 5,980,530 A | 11/1999 | Willard et al. | |
| 6,068,634 A | 5/2000 | Lorentzen Cornelius et al. | |
| 6,214,040 B1 * | 4/2001 | Jayaraman | 623/1.13 |
| 6,221,097 B1 | 4/2001 | Wang et al. | |
| 6,306,163 B1 * | 10/2001 | Fitz | 623/1.12 |
| 6,387,118 B1 * | 5/2002 | Hanson | 623/1.11 |
| 6,395,008 B1 | 5/2002 | Ellis | |
| 6,432,130 B1 | 8/2002 | Hanson et al. | |
| 6,554,841 B1 | 4/2003 | Yang et al. | |
| 6,565,595 B1 | 5/2003 | DiCaprio et al. | |
| 6,607,552 B1 | 8/2003 | Hanson et al. | |
| 6,964,676 B1 | 11/2005 | Gerberding et al. | |

* cited by examiner

*Primary Examiner* — Gary Jackson
*Assistant Examiner* — Michael Mendoza
(74) *Attorney, Agent, or Firm* — Vidas, Arrett and Steinkraus

(57) ABSTRACT

A stent delivery system which includes a stent delivery catheter, the stent delivery catheter having a stent mounting region, the stent mounting region having an inflatable portion. A stent is disposed about the stent mounting region, the stent having an unexpanded position and an expanded position. At least one stent retaining sleeve is also included having first and second ends, the first end being attached to the stent delivery catheter, the at least one stent retaining sleeve disposed about at least a portion of the stent in the unexpanded position, the stent retaining sleeve being constructed and arranged to retract toward the attached first end when the stent is expanded.

15 Claims, 2 Drawing Sheets

STENT BODY SOCK

CROSS-REFERENCE TO RELATED APPLICATIONS

This application is a Continuation Application of U.S. application Ser. No. 09/970,458, filed on Oct. 2, 2001 now abandoned, which claims the benefit of U.S. Provisional Application 60/238,795, filed on Oct. 5, 2000, both of which are incorporated herein by reference in their entireties.

STATEMENT REGARDING FEDERALLY SPONSORED RESEARCH

Not Applicable

BACKGROUND OF THE INVENTION

It is well understood that stents which are not properly secured or retained to the catheter may slip and either be lost or be deployed in the wrong location or partially deployed. Traditionally, in order to provide proper securement of the stent on the catheter the stent is crimped to a predetermined area of the catheter.

In the past, crimping has been done by hand or by a crimping apparatus, often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

The present invention avoids these problems by providing stent retaining sock(s) or sleeves which are capable of securing a stent to the catheter without the need to crimp the stent into place. The sock(s) may be utilized with nearly any type of stent. Both self-expanding and inflation expandable stents are well known and widely available in a variety of designs and configurations. Self-expanding stents must be maintained under a contained sheath or sock(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter without translocating proximally or distally and especially without becoming separated from the catheter. The stent, particularly its distal and proximal ends, must be protected to prevent distortion of the stent and to prevent abrasion and/or reduce trauma of the vessel walls. It is also important to prevent stent flaring during bending and tracking of the stent.

In light of the above, it would be desirable to employ a stent covering which functions to help retain the stent on the catheter but which could optionally be left on the catheter during stent delivery so as to avoid damaging the stent or causing undesirable movement of the stent during sheath retraction. It would be desirable to provide for a covering which is flexible and which sufficiently covers a stent so as to prevent stent elements from protruding outward from the catheter and interfering with a vessel wall prior to delivery. It would also be desirable to provide a covering which does not increase the profile of the stent delivery catheter beyond its profile without the covering.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Other patents which describe socks or sleeves, and material used therefor, include Blaeser et al. U.S. Pat. No. 5,944,726 issued Aug. 31, 1999; Dusbabek et al. U.S. Pat. No. 5,968,069, issued Oct. 10, 1999; and Cornelius et al., U.S. Pat. No. 6,068,634, issued May 30, 2000. In addition, co-pending application Ser. Nos. 08/701,979; 08/702,149; 09/273,520; 09/549,286; 09/552,807; 09/668,496; 09/664,267, and 09/664,268 all relate to stent retaining sleeves or socks.

All U.S. patents, applications and all other published documents mentioned anywhere in this application are incorporated herein by reference in their entirety.

BRIEF SUMMARY OF THE INVENTION

This invention provides an improvement over the prior art, by providing a stent delivery system which includes one or more stent retaining sleeves or socks which are constructed and arranged to retract off of the stent when the stent is expanded. The sleeves of the present invention are capable of retaining and immobilizing a non-crimped or crimped stent on the catheter surface by completely covering all or only a portion of the stent, the sleeves are readily retracted from off of the stent to provide for safe and effective stent release.

The invention may utilize a single sock or sleeve which either retracts proximally or distally, or two sleeves which each cover one end of the stent and retract axially away from each other. The socks or sleeves may be ribbed or accordion; have holes or perforations or be made of two or more materials to construct one or two socks which retract off of the stent when the stent is expanded, as disclosed in the incorporated co-pending applications set forth above. The sleeve or sleeves may be composed of an elastic polymer, a non-elastic polymer or a combination thereof.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
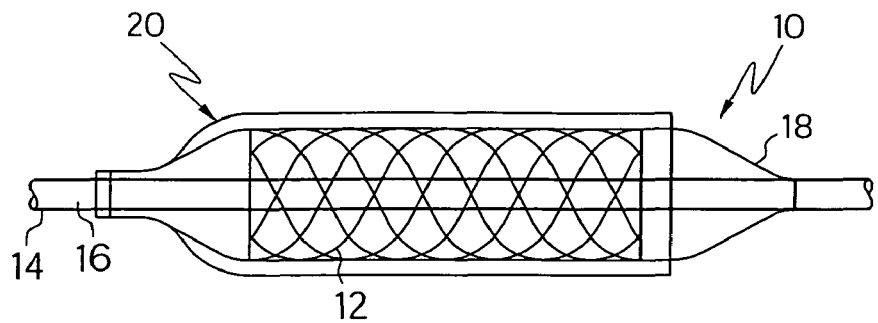
FIG. 1 is a side view of the stent delivery system showing a single sleeve attached proximally of the stent.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows a first embodiment of a stent delivery system, indicated generally at 10, which includes a stent 12 mounted upon a stent delivery catheter 14. FIG. 1 shows the stent delivery system prior to stent delivery. The stent delivery catheter 14 includes a catheter shaft 16 with and inflatable portion or balloon 18. A stent retaining sleeve 20 is engaged at a proximal portion 22 of the catheter shaft 16 adjacent to the balloon 18. The sleeve 20 extends distally over the stent 12 when in the unexpanded position. When the balloon 18 is expanded and the stent 12 expands from the unexpanded state to the expanded state, the sleeve 20 will be retracted proximally off of the stent 12 thereby allowing the stent to deploy.

Figure 2:
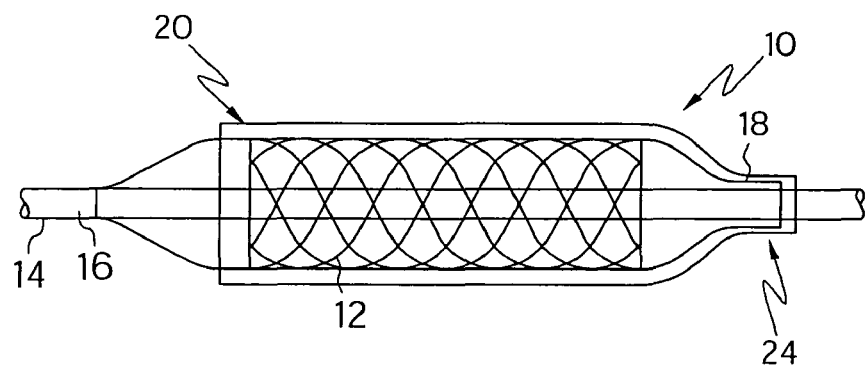
FIG. 2 is a side view of the stent delivery system showing a single sleeve attached distally of the stent.

FIG. 2, on the other hand, depicts the stent delivery system 10 having a sleeve 20 secured to a distal portion 24 of the catheter shaft 16. In the embodiment shown in FIG. 2, the sleeve 20 is retracted distally when the stent 12 is expanded from the unexpanded state to the expanded state.

Figure 3:
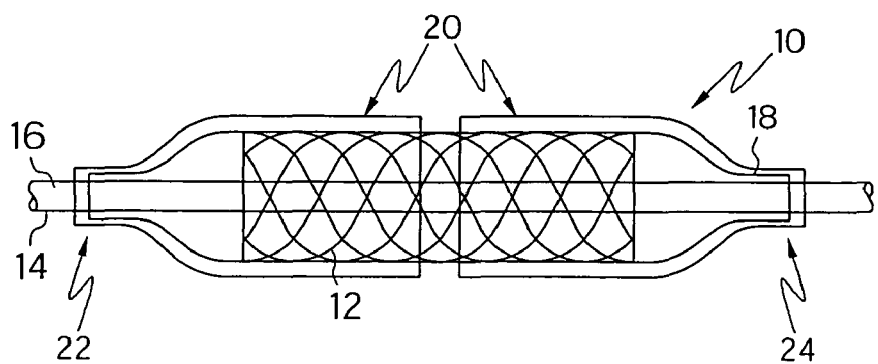
FIG. 3 is a side view of the stent delivery system showing both a proximal and distal socks, each attached on the proximal and distal sides of the stent, respectively.

FIG. 3, shows an embodiment wherein the stent delivery system employs a pair of sleeves 20. One of the sleeves 20 is engaged at the proximal portion 22 and one sleeve 20 is engaged to the distal portion 24. Unlike many prior cases, the present sleeves are constructed to cover not only the very ends of the stent 12, but as shown they may have sufficient length to overlay the entire stent or significant portions thereof. Alternatively, the sleeves 20 may be configured to overlap one another.

Figure 4:
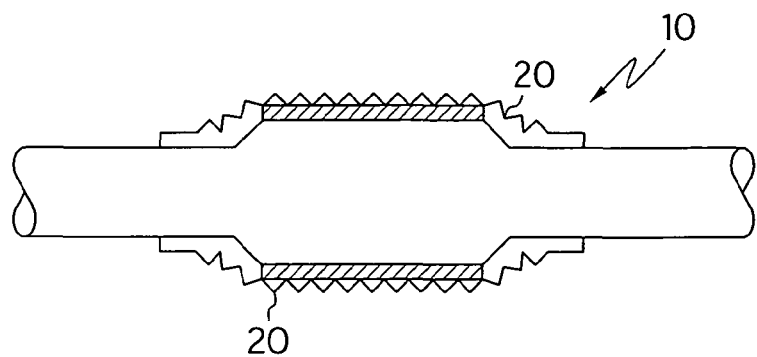
FIG. 4 is a side view of the embodiment of FIG. 3 with ribbed socks.

In FIG. 4 an alternative embodiment of the system 10 shown in FIG. 3 is shown. As illustrated in FIG. 4, the sleeves 20 may be provided with an corrugated or ribbed configuration. Such a ribbed configuration may be used for sleeve(s) 20 as shown in FIGS. 1-3 to provide the sleeve with the desired characteristics discussed above.

Figure 5:
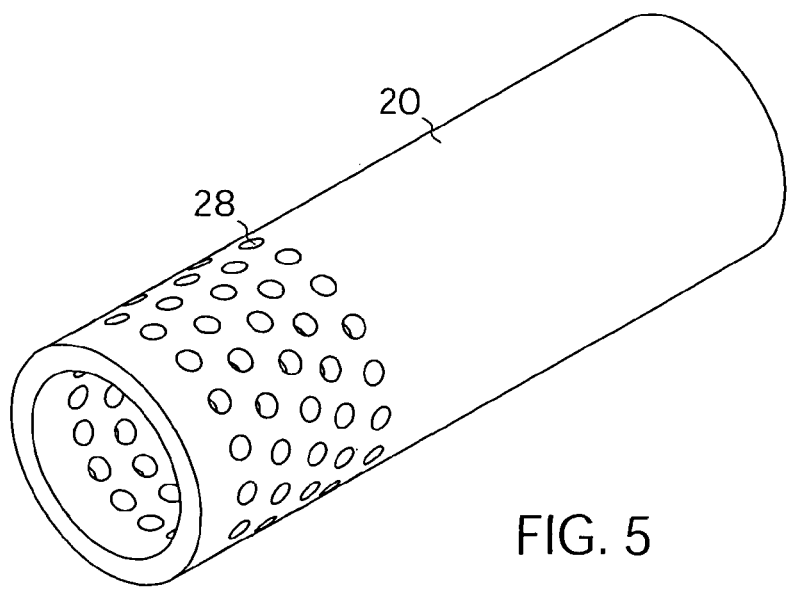
FIG. 5 is a side view of a perforated sock.

In FIG. 5 another alternative embodiment is shown. In FIG. 5, it may be seen that the sleeve 20 is equipped with a plurality of holes 28. The holes 28 may be provided to the sleeves 20 illustrated in FIGS. 1-3 to provide the sleeves 20 with the ability to retract off of the stent as desired.

Figure 6:
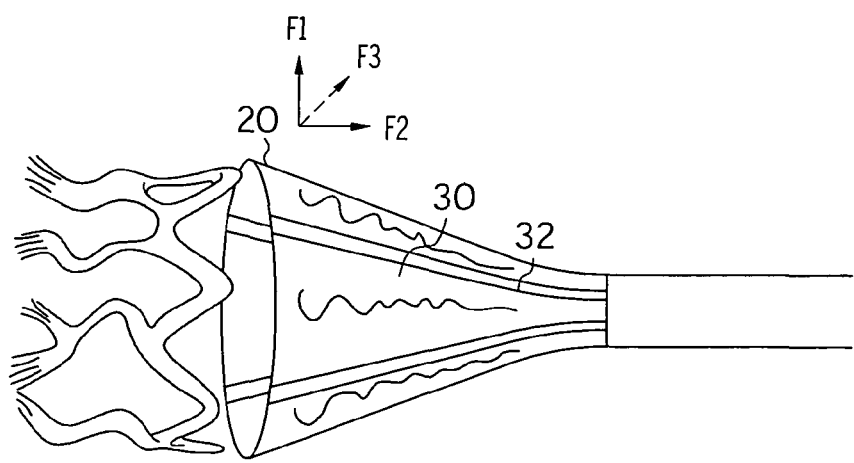
FIG. 6 is a side view of a striped sock.

In FIG. 6 yet another alternative embodiment is shown, wherein the sleeve is composed of a combination of a first material 30 and at least one additional material 32. As illustrated the materials 30 and 32 may be configured in the sleeve 20 to provide a stripped configuration. Such a sleeve may be used in any of the embodiments shown in FIGS. 1-3. In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent delivery system comprising:
    a stent delivery catheter, the stent delivery catheter having a stent mounting region, the stent mounting region having an inflatable portion;
    a stent disposed about the stent mounting region, the stent having an unexpanded state and an expanded state;
    a stent retaining sleeve having first and second ends and a body extending therebetween, the first end being attached to the stent delivery catheter adjacent to a first end of the stent mounting region, at least a portion of the stent retaining sleeve disposed about and covering the entire stent in its unexpanded state so that the second end of the stent retaining sleeve is adjacent a second end of the stent mounting region, the stent retaining sleeve being constructed and arranged to retract toward the attached first end when the stent is expanded, wherein the at least a portion of the stent retaining sleeve disposed about and covering the entire stent having an inner surface comprising first portions and second portions wherein the first portions of the inner surface are positioned closer to the outer surface of the stent than the second portions, wherein the stent retaining sleeve has a plurality of openings.

2. The stent delivery system of claim 1, wherein the stent retaining sleeve is accordion shaped.

3. The stent delivery system of claim 2, wherein, when the stent retaining sleeve is fully extended over the stent, the second end is longitudinally adjacent to the stent.

4. The stent delivery system of claim 1, wherein the stent retaining sleeve is comprised of at least two materials.

5. The stent delivery system of claim 1, wherein the first end of the stent retaining sleeve is attached proximally of the stent.

6. The stent delivery system of claim 1, wherein the sleeve is ribbed.

7. The stent delivery system of claim 1, the first end being longitudinally fixed relative to the stent mounting region, wherein, when the retaining sleeve retracts toward the attached first end when the stent is expanded, the distance between the first and second ends of the stent retaining sleeve is shortened.

8. The stent delivery system of claim 1, wherein the first and second portions of the inner surface alternate with one another.

9. A stent delivery system comprising:
    a stent delivery catheter, the stent delivery catheter having a stent mounting region, the stent mounting region having an inflatable portion;
    a stent disposed about the stent mounting region, the stent having an unexpanded state and an expanded state;
    a stent retaining sleeve having a circumference and first and second ends with a body extending between the first and second ends, the first end being attached to the stent delivery catheter adjacent to a first end of the stent mounting region, at least a portion of the stent retaining sleeve disposed about and covering the entire stent in its unexpanded state so that the second end of the stent retaining sleeve is adjacent a second end of the stent mounting region, the stent retaining sleeve being constructed and arranged to retract toward the attached first end when the stent is expanded, wherein the at least the portion of the stent retaining sleeve comprises a plurality of pleats when disposed about and covering the stent, wherein each pleat extends about the circumference of the sleeve, wherein the stent retaining sleeve has a plurality of openings.

10. The stent delivery system of claim 9, wherein the first end of the stent retaining sleeve is attached proximally of the stent.

11. The stent delivery system of claim 9, the at least a portion of the stent retaining sleeve disposed about and covering the entire stent having an inner surface comprising first portions and second portions, and an outer surface, wherein the first portions of the inner surface are positioned closer to the outer surface of the stent than the second portions.

12. The stent delivery system of claim 9, the first end being longitudinally fixed relative to the stent mounting region, wherein, when the retaining sleeve retracts toward the attached first end when the stent is expanded, the distance between the first and second ends of the stent retaining sleeve is shortened.

13. A stent delivery system comprising:
a stent delivery catheter, the stent delivery catheter having a stent mounting region, the stent mounting region having an inflatable portion;
a stent disposed about the stent mounting region, the stent having an unexpanded state and an expanded state;
a stent retaining sleeve having first and second ends, wherein the stent retaining sleeve is a single layer, the first end being attached to the stent delivery catheter adjacent to the stent mounting region, the stent retaining sleeve disposed about and covering the entire stent in its unexpanded state, the stent retaining sleeve being constructed and arranged to retract toward the attached first end when the stent is expanded, wherein the stent retaining sleeve is comprised of at least two materials, wherein the stent retaining sleeve is comprised of alternating strips of the at least two materials, and wherein each strip of material extends from the first end of the sleeve to the second end of the sleeve, wherein the stent retaining sleeve has a plurality of openings.

14. The stent delivery system of claim 13, wherein the first end of the stent retaining sleeve is attached proximally of the stent.

15. The stent delivery system of claim 13, the first end being longitudinally fixed relative to the stent mounting region, wherein, when the retaining sleeve retracts toward the attached first end when the stent is expanded, the distance between the first and second ends of the stent retaining sleeve is shortened.

* * * * *